| United States Patent [19]
Payne

[11] Patent Number: 5,716,703
[45] Date of Patent: Feb. 10, 1998

[54] FLUID ACQUISITION AND DISTRIBUTION MEMBER FOR ABSORBENT CORE

[75] Inventor: Michael Payne, Cincinnati, Ohio

[73] Assignee: The Procter & Gamble Company, Cincinnati, Ohio

[21] Appl. No.: 678,149

[22] Filed: Jul. 11, 1996

Related U.S. Application Data

[60] Continuation of Ser. No. 469,477, Jun. 6, 1995, abandoned, which is a division of Ser. No. 210,831, Mar. 18, 1994, abandoned.

[51] Int. Cl.$^6$ .................................................. D21H 11/20
[52] U.S. Cl. ...................... 428/378; 162/157.6; 428/393; 524/35; 524/321; 524/377; 525/54.21; 536/56; 604/378
[58] Field of Search ............ 525/54.21; 536/56; 524/35, 321, 377; 428/378, 393; 604/378; 162/157.6

[56] References Cited

U.S. PATENT DOCUMENTS 5,217,445  6/1993  Young et al. ..................... 604/381
5,399,240  3/1995  Graef et al. ...................... 162/182

FOREIGN PATENT DOCUMENTS 4002648  6/1987  Japan .

*Primary Examiner*—Andrew E. C. Merriam
*Attorney, Agent, or Firm*—Bart S. Hersko; E. Kelly Linman; Jacobus C. Rasser

[57] ABSTRACT

Skin wetness is minimized on overnight usage of a disposable absorbent article containing an acquisition and distribution member consisting essentially of $C_2$–$C_9$ polycarboxylic acid crosslinked cellulosic fibers prepared in the presence of surfactant.

7 Claims, 2 Drawing Sheets

FLUID ACQUISITION AND DISTRIBUTION MEMBER FOR ABSORBENT CORE

This application is a continuation of application Ser. No. 08/469,477, filed Jun. 6, 1995, now abandoned, which is a divisional application of application Ser. No. 08/210,831 filed Mar. 18, 1994, now abandoned.

TECHNICAL FIELD

This invention relates to disposable absorbent articles using polycarboxylic acid $C_2$–$C_9$ crosslinked cellulosic fibers. Exemplary of the absorbent articles are disposable diapers, training pants, adult incontinent pads and sanitary napkins.

BACKGROUND OF THE INVENTION

Consideration has been given to including fluid acquisition and distribution elements in disposable absorbent articles with a goal of minimizing the occurrence of prolonged skin wetness to negate this as a factor for producing skin irritation, e.g., diaper rash.

Weisman et al., U.S. Pat. No. 4,673,402, teaches an absorbent core with an upper fluid acquisition/distribution layer which consists essentially of hydrophilic fiber material, preferably wood pulp fibers and wood pulp tissue, and a lower fluid storage layer consisting essentially of a substantially uniform combination of hydrophilic fiber material and particular amounts of discrete particles of substantially water-insoluble, fluid-absorbing hydrogel material and placed toward the front of the absorbent article.

Meyer et al., U.S. Pat. No. 4,798,603, teaches an absorbent article with a transport layer between a topsheet and an absorbent body wherein the transport layer is less hydrophilic than the absorbent body material and may be a nonwoven fibrous web composed of substantially hydrophobic material, such as polypropylene, polyethylene or polyester, which may be treated with selected amount of surfactant to increase its initial wettability.

Alemany et al., U.S. Pat. No. 4,834,735, teaches an absorbent member with an acquisition zone and a storage zone laterally surrounding its perimeter, with the acquisition zone having a lower average density and a lower average basis weight per unit area than the storage zone. The absorbent member comprises a mixture of hydrophilic fibrous material and discrete particles of absorbent gelling material.

Lash et al., U.S. Pat. No. 4,935,022, teaches a disposable absorbent article with an absorbent core composed of an upper fluid acquisition/distribution layer of stiffened cellulose fibers and from about 3 to 15% by weight absorbent gelling material, and a lower fluid storage layer having a top surface area smaller in area than the top surface area of the fluid acquisition/distribution layer and composed of stiffened cellulose fibers and from about 15 to 60% by weight of absorbent gelling material.

Reising U.S. Pat. No. 4,988,345, teaches a storage layer comprising hydrophilic fibrous material and discrete particles of absorbent gelling material, containing an acquisition aperture.

Young et al., U.S. Pat. No. 5,217,445, teaches an absorbent core comprising an upper, wetlaid, fluid acquisition/distribution layer comprising from about 50% to 100% stiffened fibers and a lower fluid storage area comprising at least 15% by weight superabsorbent material, with the fluid acquisition/distribution layer having a top surface of lesser area than the top surface of the fluid storage area.

In the course of experiments leading to the invention herein, the $C_2$–$C_9$ polycarboxylic acid crosslinked cellulosic fibers that are the subject of Herron et al., U.S. Pat. No. 5,137,537 were used as stiffened fibers in a fluid acquisition and distribution member in absorbent cores in disposable diapers. About 10% of babies, on overnight usage of these diapers, were found to experience skin wetness.

SUMMARY OF THE INVENTION

It has been discovered herein that skin wetness is minimized on a sustained basis when the acquisition and distribution member comprises $C_2$–$C_9$ polycarboxylic acid crosslinked cellulosic fibers containing surface active agent thereon, preferably surface active agent that is applied to cellulosic fibers prior to the crosslinking reactions being carried out.

The fluid acquisition and distribution member herein is for use in a disposable absorbent article and has a dry density ranging from 0.03 to 0.20 g/cc and consists essentially of individualized, crosslinked cellulosic fibers having an amount of a $C_2$–$C_9$ polycarboxylic acid crosslinking agent reacted therein in an intrafiber ester crosslink bond form to provide a water retention value of from about 25 to 60, and having substantially uniformly distributed thereon from about 0.005 to 1%, by weight, preferably up to about 0.15%, by weight, on a dry fiber basis, of surface active agent. Preferably, the surface active agent is a nonionic surfactant, and is very preferably a nonionic surfactant formed by condensing ethylene oxide with a hydrophobic base formed by condensation of propylene oxide with propylene glycol, having an average molecular weight ranging from about 1,000 g/mole to 5,000 g/mole, a molecular weight of poly (oxypropylene) hydrophobe ranging from 900 g/mole to 2,000 g/mole, and from 10 to 80% of poly(oxyethylene) hydrophilic unit by weight in the total molecule; most preferably having an average molecular weight of 1,900 g/mole, a molecular weight of poly(oxypropylene) hydrophobe of 950 g/mole, and 50% poly(oxyethylene) hydrophilic unit by weight in the total molecule (available under the Trade Name Pluronic® L35).

The individualized, crosslinked cellulosic fibers with surface active agent thereon are very preferably prepared by a process comprising heating uncrosslinked cellulosic fibers with from 1% to 15%, preferably from 3% to 12%, by weight on a citric acid basis, applied on a dry fiber basis, of $C_2$–$C_9$ polycarboxylic acid crosslinking agent, and from 0.005% to 1%, preferably from 0.01% to 0.2%, by weight, applied on a dry fiber basis, of surface active agent thereon, to remove any moisture content and to cause the polycarboxylic acid crosslinking agent to react with the cellulosic fibers and form ester crosslinks between cellulose molecules, i.e., to cause curing, to form said crosslinked cellulosic fibers with surface active agent thereon, without washing of the crosslinked fibers or bleaching and washing of the crosslinked fibers.

The disposable absorbent article herein, e.g., a disposable diaper, training pants, adult incontinent pad or sanitary napkin, comprises a liquid pervious topsheet, liquid impervious backsheet and an absorbent core positioned between the topsheet and the backsheet. The absorbent core comprises (i) the fluid acquisition and distribution member herein with a top surface positioned adjacent said topsheet and a bottom surface and (ii) a fluid storage member (i.e., a fluid retention member) having a top surface in contact with the bottom surface of the fluid acquisition and distribution member and comprising absorbent gelling material.

Preferably, the fluid acquisition and distribution member has a top surface with an area which is less than the area of the top surface of the fluid storage member, very preferably which has a top surface with an area which is about 15% to 95% of the top surface of the fluid storage member, most preferably a top surface with an area which is about 20% to 50% of the top surface of the fluid storage member.

The term "individualized, crosslinked fibers" is used herein to mean that crosslinks are primarily intrafiber rather than interfiber.

The term "intrafiber" means that a polycarboxylic acid molecule is reacted only with a molecule or molecules of a single fiber rather than between molecules of separate fibers.

The mole % of polycarboxylic acid crosslinking agent, calculated on a cellulose anhydroglucose molar basis, reacted with the fibers is determined by the following procedure: A sample of the crosslinked fibers is first washed with sufficient hot water to remove any unreacted crosslinking agent and catalysts. Next, the fibers are dried to equilibrium moisture content, Then, the free carboxyl group content is determined essentially in accordance with T.A.P.P.I. method T237 OS-77. The mole % of reacted polycarboxylic acid crosslinking agent is then calculated based on the assumptions that one carboxyl group is left unreacted in each molecule of polycarboxylic acid, that the fibers before reaction have a carboxyl content of 30 meq/kg, that no new carboxyls are generated on cellulose molecules during the crosslinking process apart from the free carboxyls on crosslinking moieties, and that the molecular weight of the crosslinked pulp fibers is 162 (i.e., one anhydroglucose unit).

The term "ester crosslink bond" is used herein to mean that the polycarboxylic acid crosslinking agents react with hydroxyl groups of fiber component molecules to form ester bonds.

The term "citric acid basis" is used herein to mean the weight of citric acid providing the same number of reacting carboxyl groups as are provided by the polycarboxylic acid actually used, with the reacting carboxyl groups being the reactive carboxyl groups less one per molecule. The term "reactive carboxyl groups" is defined later.

The term "applied on a dry fiber basis" means that the percentage is established by a ratio wherein the denominator is the weight of cellulosic fibers present if they were dry (i.e., no moisture content).

The "water retention values" set forth herein are determined by the following procedure: A sample of about 0.3 g to about 0.4 g of fibers (i.e., about a 0.3 g to about a 0.4 g portion of the fibers for which water retention value is being determined) is soaked in a covered container with about 100 ml distilled or deionized water at room temperature for between about 15 and about 20 hours. The soaked fibers are collected on a filter and transferred to an 80-mesh wire basket supported about 1½ inches above a 60-mesh screened bottom of a centrifuge tube. The tube is covered with a plastic cover and the sample is centrifuged at a relative centrifuge force of 1,500 to 1,700 gravities for 19 to 21 minutes. The centrifuged fibers are then removed from the basket and weighed. The weighed fibers are dried to a constant weight at 105° C. and reweighed. The water retention value (WRV) is calculated as follows:

$$WRV = \frac{(W-D)}{D} \times 100$$

where,

W=wet weight of the centrifuged fibers;
D=dry weight of the fibers; and
W−D=weight of absorbed water.

The water retention value remains the same regardless of whether or not the fibers have surface active agent distributed thereon in the amounts applicable to the invention herein.

The 5K density test herein is a measure of fiber stiffness and of dry resiliency of a structure made from the fibers (i.e., ability of the structure to expand upon release of compressional force applied while the fibers are in substantially dry condition), and is carried out according to the following procedure. A four inch by four inch square air-laid pad having a mass of about 7.5 g is prepared from the fibers for which dry resiliency is being determined, and compressed, in a dry state, by a hydraulic press to a pressure of 5,000 psi, and the pressure is quickly released. The pad is inverted and the pressing is repeated and released. The thickness of the pad is measured after pressing with a no-load caliper (Ames thickness tester). Five thickness readings are taken, one in the center and 0.001 inches in from each of the four corners and the five values are averaged. The pad is trimmed to 4 inches by 4 inches and then is weighed. Density after pressing is then calculated as mass/(area×thickness). This density is denoted the 5K density herein. The lower the values in the 5K density test, i.e., the density after pressing, the greater the fiber stiffness and the greater the dry resiliency.

The drip capacity test herein is a combined measure of absorbent capacity and absorbency rate and is carried out herein by the following procedure: A four inch by four inch square air-laid pad having a mass of about 7.5 g is prepared from the fibers for which drip capacity is being determined and is placed on a screen mesh. Synthetic urine is applied to the center of the pad at a rate of 8 ml/s. The flow of synthetic urine is halted when the first drop of synthetic urine escapes from the bottom or sides of the pad. The drip capacity is the difference in mass of the pad prior to and subsequent to introduction of the synthetic urine divided by the mass of the fibers, bone dry basis. The greater the drip capacity is, the better the absorbency properties.

The wicking rate test herein is a measure of the rate at which liquid wicks through a pad of fibers being tested and is determined herein by the following procedure: A four inch by four inch square air laid pad having a mass of about 3.5 g and a density of 0.2 g/cc is prepared from the fibers for which wicking rate is being determined. The test is carried out in a wicking rate tester. The wicking rate tester comprises a container, two lower electrodes with pins for inserting through a sample, two upper electrodes with pins for inserting through a sample, two vertically oriented plates for positioning in the container, and a timer controlled to start when any of the two adjacent pins on the lower electrodes are contacted by liquid and to stop when any two adjacent pins on the upper electrodes are contacted by liquid. Synthetic urine is placed in the container of the wicking rate tester to provide a depth of 1 inch of synthetic urine therein. The pad of fibers being tested is placed between the plates of the wicking rate tester with the pins of the lower electrodes being inserted through the entire thickness of the pad 7/12 inch from the bottom of the pad and the pins of the upper electrodes being inserted through the entire thickness of the pad 2¹/12 inch from the bottom of the pad and the assembly is inserted into the body of synthetic urine in the container of the tester so that the bottom ⅓ inch of the pad extends into the synthetic urine. The wicking rate in cm/s is 3.81 (the distance between the upper and lower electrodes in cm)

divided by the time to wick from the lower electrodes in the upper electrodes as indicated by the timer. The larger the wicking rate, the faster the wicking.

The wet compressibility test herein is a measure of wet responsiveness and absorbency in a structure made from the fibers for which the property is being determined and is carried out by the following procedure: An air laid four by four inch square pad weighing about 7.5 g is prepared from the fibers being tested. The density of the pad is adjusted to 0.2 g/cc with a press. The pad is loaded with synthetic urine to ten times its dry weight or to its saturation point, whichever is less. A 0.1 PSI compressional load is applied to the pad. After about 60 seconds, during which time the pad equilibrates, the compressional load is then increased to 1.1 PSI. The pad is allowed to equilibrate, and the compressional load is then reduced to 0.1 PSI. The pad is then allowed to equilibrate, and the thickness is measured. The density is calculated for the pad at the second 0.1 PSI load, i.e., based on the thickness measurement after the pad equilibrates after the compressional load is reduced to 0.1 PSI. The void volume, reported in cc/g, is then determined. The void volume is the reciprocal of the wet pad density minus the fiber volume (0.95 cc/g). This void volume is denoted the wet compressibility herein. Higher values indicate greater wet responsiveness.

The leakage rate test herein is a measure of the percentage of the cases of babies experiencing leakage on overnight usage and is carried out by the following procedure: Medium size Pampers® are modified to include a rectangular fluid acquisition and distribution member of 3 inches by 10 inches by about one-fourth inch between the topsheet and the fluid absorbent core, with the leading edge of the width of the fluid acquisition and distribution member being positioned 2 to 3 inches below the front waist of the diaper. The modified product is given to mothers of 20 male babies normally wearing medium size disposable diapers. The mothers employ the diapers for overnight usage and check the babies on awaking in the morning and report whether the babies experience leakage. The results are reported in percentage of babies completing the test who are found to experience leakage when checked after overnight usage.

The skin wetness test herein is a measure of the percentage of the cases of babies found to be wet after overnight usage and is carried out by the following procedure: Medium size Pampers® are modified to include a rectangular fluid acquisition and distribution member of 3 inches by 10 inches by about one-fourth inch between the topsheet and the fluid absorbent core with the leading edge of the widths of the fluid acquisition and distribution member being positioned 2 to 3 inches below the front waist of the diaper. The modified product is given to mothers of 20 male babies normally wearing medium size disposable diapers. The mothers employ the diapers for overnight usage and check the babies on awakening in the morning and report whether the babies are wet. The results are reported in percentage of babies completing the test who are found to be wet when checked after overnight usage.

The gush capacity test herein is a measure of how much fluid is immediately released to the base core of a diaper through the acquisition and distribution member upon loading and how much fluid remains in the acquisition and distribution member after the diaper has allowed to equilibrate and is carried out by the following procedure: Two medium size Pampers® diapers are used in each test. The top sheets are removed and the diapers are placed with the baby side facing up. The fluid acquisition and distribution members tested are rectangular in top view and are 3 inches by 10 inches by about one-fourth inch with the leading edge of the width of the fluid acquisition and distribution member being positioned 2 to 3 inches below the front waist of the diaper. Synthetic urine is metered onto the center of the top surface fluid acquisition and distribution member through a tube with its outlet opening positioned about 3 inches above top surface of the fluid acquisition and distribution member at its center. Synthetic urine is metered onto the top surface of the fluid acquisition and distribution member in batches of 50 ml at the rate of 10 ml per second. One of the fluid acquisition and distribution members is removed immediately after the 50 ml of fluid has been loaded and is weighed and then is returned to the diaper. The other is allowed to remain untouched for 15 minutes so that fluid is allowed to drain for this period, and is then removed and weighed to determine the final amount of fluid remaining therein prior to the loading of another 50 ml of synthetic urine and then is returned to the diaper for the loading of another 50 ml of synthetic urine. This procedure is then repeated with 50 ml more of synthetic urine. This is continued until a total of 400 ml of synthetic urine is added, with measurements carried out as described above with each 50 ml loading. Lower values on the initial measurements indicate faster acquiring. Lower values at the 15 minute measurements indicate faster partitioning (i.e., faster transfer of fluid from one layer to another when the two layers are in contact).

The acquisition rate test herein is a measure of the rapidness of acquisition and of the amount of acquisition over time and is carried out by the following procedure: Medium size Pampers® are modified to include a rectangular top view fluid acquisition and distribution member of 3 inches by 10 inches by about one-fourth inch between the top sheet and the fluid absorbent core with the leading edge of the width of the fluid acquisition and distribution member being positioned 2 to 3 inches below the front waist of the diaper. The modified diaper is placed on a piece of foam on the tester base, with the baby side of the diaper facing up. A cylinder of about 1¾ inch diameter which is open at the top and bottom is placed against the top surface of the topsheet above the center of the fluid acquisition and distribution member. A weight is applied to provide a pressure of 0.4 psi to the top surface of the remainder of the topsheet. Four loadings of 50 ml of synthetic urine are metered into the cylinder, each at a rate of 5 ml/sec with a 5 minute equilibration time allowed for each loading, i.e., the four loadings are each applied 5 minutes apart so that the total time of the test is about 20 minutes. The acquisition time is measured for each loading (i.e., the time between initiation of metering and when the fluid disappears from the cylinder), and the acquisition rate in ml/sec is calculated at each loading by dividing the 50 ml by the acquisition time. Then the acquisition potential Ao and acquisition rate constant K are calculated using the equation $$\ln A = (-1/K)(L) + \ln Ao$$

where A is the acquisition rate in ml/sec of 50 ml of fluid, Ao is the acquisition potential, L is the cumulative load, K is the acquisition constant (theoretical load at which about half of the acquisition potential is reached), A and L are from data, and Ao and K are calculated. The higher the value for Ao, the more rapid the acquisition will be. The higher the value for K, the greater the acquisition over time.

The term "synthetic urine" is used herein to mean solution prepared from tap water and 10 grams of sodium chloride per liter of tap water and 0.51 ml of a 1.0% aqueous solution of Triton X100 (an octylphenoxy polyethoxy ethanol surfactant, available from Rohm & Haas Co.) per liter of tap water. The synthetic urine should be at 25±1% °C. when it is used.

The term "upper" is used herein in relation to an absorbent core to mean the portion of the absorbent core nearest to the article topsheet, and the term "lower" is used herein in relation to an absorbent core to mean the portion of the absorbent core nearest to the article backsheet.

The density values herein are calculated from basis weight and layer caliper measured under a confining pressure of 0.2 psi (1.43 kPa).

The air laid pads referred to herein are made as follows: Air laying is carried out to air lay approximately 120 g of fibers into a 14" by 14" square on a piece of tissue and a second piece of tissue is then placed on top of the air laid mass to form a pad. The pad is pressed and cut into 4" by 4" squares.

The terms "defibration" and "defibrating" are used herein to refer to any procedure which may be used to mechanically separate fibers into substantially individual form even though they are already in such form, i.e., to the step(s) of mechanically treating fibers in either individual form or in more compacted form, where the treating (a) separates the fibers into substantially individual form if they were not already in such form and/or (b) imparts curl and twist to the fibers in dry state.

DETAILED DESCRIPTION

Figure 1:
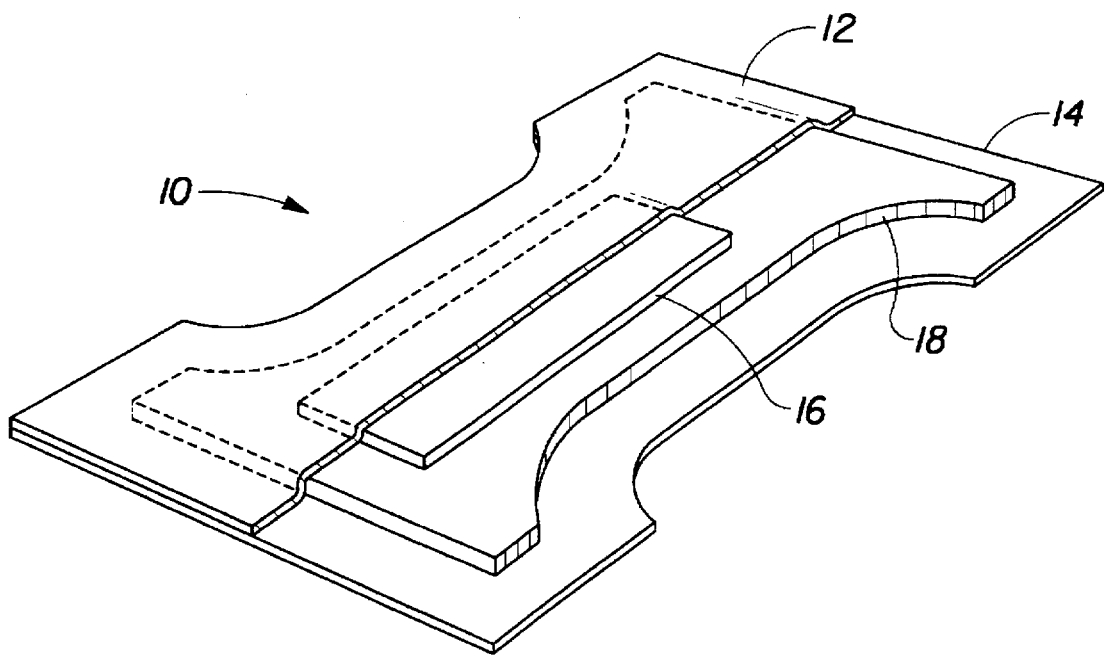
FIG. 1 represents a perspective view of a disposable diaper of the present invention.

We turn first to the fluid acquisition and distribution member herein.

As previously indicated, it has a dry density ranging from 0.03 to 0.20 g/cc and consists essentially of individualized, crosslinked cellulosic fibers having an amount of a $C_2$–$C_9$ polycarboxylic acid crosslinking agent reacted therein in an intrafiber ester crosslink bond form to provide a water retention value of from about 25 to 60, and having substantially uniformly distributed thereon from about 0.0005% to 1%, by weight, on a dry fiber basis, of surface active agent. U.S. Pat. No. 5,137,537 indicates that the amount of $C_2$–$C_9$ polycarboxylic acid crosslinking agent reacted with the fibers providing a water retention value of from about 25 to 60 may be about 0.5 mole percent to about 10 mole percent, calculated on a cellulose anhydroglucose molar basis.

Preferably, it has a dry density ranging from 0.06 to 0.08 g/cc.

It is preferably substantially free of any component that interferes with the ability of the member to distribute fluid (e.g., urine or menses) to an adjacent hydrophilic layer (e.g., a fluid storage area).

Preferably, the crosslinked cellulose fibers have an amount of $C_2$–$C_9$ polycarboxylic acid crosslinking agent reacted therein in an intrafiber ester crosslink bond form to provide a water retention value ranging from 28 to 50.

As previously indicated, the surface active agent is preferably present on the fibers in an amount of up to about 0.15%, by weight, on a dry fiber basis, i.e., in an amount ranging from 0.0005% to 0.15%, by weight, on a dry fiber basis. Very preferably, the surface active agent is present on the fibers in an amount ranging from about 0.001% to 0.20%, by weight, on a dry fiber basis.

We turn now to the cellulosic fibers which are subjected to crosslinking to provide the individualized, crosslinked cellulosic fibers herein. Cellulosic fibers of diverse natural origin are useful. Digested fibers from softwood, hardwood or cotton linters are preferably utilized. Fibers from Esparto grass, bagasse, hemp, flax, and other lignaceous and cellulosic fiber sources may also be utilized. Typically, the fibers are wood pulp fibers made by chemical pulping processes. Fibers from southern softwood pulp are especially preferred.

We turn now to the $C_2$–$C_9$ polycarboxylic acid crosslinking agents. These are organic acids containing two or more carboxyl (COOH) groups and from 2 to 9 carbon atoms in the chain or ring to which the carboxyl groups are attached; the carboxyl groups are not included when determining the number of carbon atoms in the chain or ring (e.g., 1,2,3 propane tricarboxylic acid would be considered to be a $C_3$ polycarboxylic acid containing three carboxyl groups and 1,2,3,4 butanetetracarboxylic acid would be considered to be a $C_4$ polycarboxylic acid containing four carboxyl groups). More specifically, the $C_2$–$C_9$ polycarboxylic acids suitable for use as crosslinking agents in the present invention include aliphatic and alicyclic acids either saturated or olefinically unsaturated, with at least three and preferably more carboxyl groups per molecule or with two carboxyl groups per molecule if a carbon—carbon double bond is present alpha, beta to one or both carboxyl groups. An additional requirement is that to be reactive in esterifying cellulose hydroxyl groups, a given carboxyl group in an aliphatic or alicyclic polycarboxylic acid must be separated from a second carboxyl group by no less than 2 carbon atoms and no more than three carbon atoms. Without being bound by theory, it appears from these requirements that for a carboxyl group to be reactive, it must be able to form a cyclic 5- or 6-membered anhydride ring with a neighboring carboxyl group in the polycarboxylic acid molecule. Where two carboxyl groups are separated by a carbon—carbon double bond or are both connected to the same ring, the two carboxyl groups must be in the cis configuration relative to each other if they are to interact in this manner. Thus a reactive carboxyl group is one separated from a second carboxyl group by no less than 2 carbon atoms and no more than 3 carbon atoms and where two carboxyl groups are separated by a carbon—carbon double bond or are both connected to the same ring, a reactive carboxyl group must be in cis configuration to another carboxyl group.

In aliphatic polycarboxylic acids containing three or more carboxyl groups per molecule, a hydroxyl group attached to a carbon atom alpha to a carboxyl group does not interfere with the esterification and crosslinking of the cellulosic fibers by the acid. Thus, polycarboxylic acids such as citric acid (also known as 2-hydroxy-1,2,3 propane tricarboxylic acid) and tartrate monosuccinic acids are suitable as crosslinking agents in the present invention.

The aliphatic or alicyclic $C_2$–$C_9$ polycarboxylic acid crosslinking agents may also contain an oxygen or sulfur atom(s) in the chain or ring to which the carboxyl groups are attached. Thus, polycarboxylic acids such as oxydisuccinic acid also known as 2,2'-oxybis(butanedioic acid), thiodisuccinic acid, and the like, are meant to be included within the scope of the invention. For purposes of the present invention, oxydisuccinic acid would be considered to be a $C_4$ polycarboxylic acid containing four carboxyl groups.

Examples of specific polycarboxylic acids which fall within the scope of this invention include the following: maleic acid, citraconic acid also known as methylmaleic acid, citric acid, itaconic acid also known as methylenesuccinic acid, tricarboxylic acid also known as 1,2,3 propane tricarboxylic acid, transaconitic acid also known as trans-1-propene-1,2,3-tricarboxylic acid, 1,2,3,4- butanetetracarboxylic acid, all-cis-1,2,3,4-cyclopentanetetracarboxylic acid, mellitic acid also known as benzenehexacarboxylic acid, and oxydisuccinic acid also known as 2,2'-oxybis(butanedioic acid). The above list of specific polycarboxylic acids is for exemplary purposes only, and is not intended to be all inclusive. Importantly, the crosslinking agent must be capable of reacting with at least two hydroxyl groups on proximately located cellulose chains in a single cellulosic fiber.

Preferably, the $C_2$–$C_9$ polycarboxylic acids used herein are aliphatic, and saturated, and contain at least three carboxyl groups per molecule. One group of preferred polycarboxylic acid agents for use with the present invention includes citric acid also known as 2-hydroxy-1,2,3 propane tricarboxylic acid, 1,2,3 propane tricarboxylic acid, and 1,2,3,4 butane tetracarboxylic acid. Citric acid is especially preferred, since it has provided fibers with high levels of wettability, absorbency and resiliency, which are safe and non-irritating to human skin, and has provided stable, crosslink bonds. Furthermore, citric acid is available in large quantities at relatively low prices, thereby making it commercially feasible for use as the crosslinking agent.

Another group of preferred crosslinking agents for use in the present invention includes saturated $C_2$–$C_9$ polycarboxylic acids containing at least one oxygen atom in the chain to which the carboxyl groups are attached. Examples of such compounds include oxydisuccinic acid, tartrate monosuccinic acid having the structural formula:

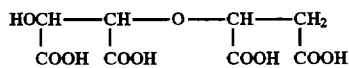

and tartrate disuccinic acid having the structural formula:

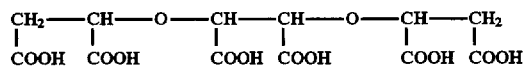

A more detailed description of tartrate monosuccinic acid, tartrate disuccinic acid, and salts thereof, can be found in Bushe et al., U.S. Pat. No. 4,663,071, issued May 5, 1987, incorporated herein by reference.

Those knowledgeable in the area of polycarboxylic acids will recognize that the aliphatic and alicyclic $C_2$–$C_9$ polycarboxylic acid crosslinking agents described above may be reacted in a variety of forms to form the crosslinked fibers used herein, such as the free acid form, and salts thereof. Although the free acid form is preferred, all such forms are meant to be included within the scope of the invention.

We turn now to the surface active agents. The surface active agent distributed on the crosslinked cellulosic fibers can be a water-soluble nonionic, ampholytic, zwitterionic, anionic or cationic surfactants or of combinations of these. Nonionic surfactants are preferred. Preferred surface active agents of one group (sold under the Trade Name Pluronic® and described hereinafter) provide a surface tension at a level of 0.1% in water at 25° C. ranging from 42 to 53 dynes/cm. Preferred surface active agents of another group (sold under the Trade Name Neodol® and described hereinafter) provide a surface tension at a level of 0.1% in water at 76° F. of 28 to 30 dynes/cm.

One class of nonionic surfactants consists of polyoxyethylene-polyoxypropylene polymeric compounds based on ethylene glycol, propylene glycol, glycerol, trimethylolpropane or ethylenediamine as the initiator reactive hydrogen compound. Preferred surfactants of this class are the compounds formed by condensing ethylene oxide with a hydrophobic base formed by the condensation of propylene oxide with propylene glycol. The average molecular weight of the surfactant normally ranges from about 1,000 to 15,000 g/mole and the molecular weight of the hydrophobic portion generally falls in the range of about 900 to 4,000 g/mole. Preferably, the surfactant average molecular weight ranges from about 1,000 to 5,000 g/mole, the molecular weight of the poly(oxypropylene) hydrophobe ranges from 900 to 2,000 g/mole and the poly(oxyethylene) hydrophilic unit is present in an amount ranging from 10% to 80% by weight of the total molecule. Such synthetic nonionic surfactants are available on the market under the Trade Name of Pluronic® and are supplied by Wyandotte Chemicals Corporation. Especially preferred nonionic surfactants are Pluronic® L31 (surfactant average molecular weight of 1,100 g/mole, molecular weight of the poly(oxypropylene) hydrophobe of 950 g/mole, and 10% poly(oxyethylene) hydrophilic unit by weight in the total molecule), Pluronic® L35 (average molecular weight of 1,900 g/mole, molecular weight of the poly(oxypropylene) hydrophobe of 950 g/mole and 50% poly(oxyethylene) hydrophilic unit by weight in the total molecule), Pluronic® L62 (surfactant average molecular weight of 2,500 g/mole, molecular weight of the poly(oxypropylene) hydrophobe of 1,750 g/mole and 20% poly(oxyethylene) hydrophilic unit by weight in the total molecule) and Pluronic® F38 (surfactant average molecular weight of 4,700 g/mole, molecular weight of the poly(oxypropylene) hydrophobic of 950 g/mole, 80% poly(oxyethylene) hydrophilic unit by weight in the total molecule). Surface tensions for 0.1% aqueous solutions of these surfactants at 25° C. are as follows: Pluronic® L31, 46.9 dynes/cm; Pluronic® L35, 48.8 dynes/cm; Pluronic® L62, 42.8 dynes/cm; Pluronic® F38, 52.2 dynes/cm. Pluronic® L35 is most preferred.

Another class of nonionic surfactants consists of the condensation products of primary or secondary aliphatic alcohols or fatty acids having from 8 to 24 carbon atoms, in either straight chain or branched chain configuration, with from 2 to about 50 moles of ethylene oxide per mole of alcohol. Preferred are aliphatic alcohols comprising between 12 and 15 carbon atoms with from about 5 to 15, very preferably from about 6 to 8, moles of ethylene oxide per mole of aliphatic compound. The preferred surfactants are prepared from primary alcohols which are either linear such as those derived from natural fats or, prepared by the Ziegler process from ethylene, e.g., myristyl, cetyl, stearyl alcohols, e.g., Neodols (Neodol being a Trade Name of Shell Chemical Company) or partly branched such as the Lutensols (Lutensol being a Trade Name of BASF) and Dobanols (Dobanol being a Trade Name of Shell) which have about 25% 2-methyl branching, or Synperonics, which are understood to have about 50% 2-methyl branching (Synperonic being a Trade Name of I.C.I.) or the primary alcohols having more than 50% branched chain structure sold under the Trade Name Lial by Liquichimica. Specific examples of nonionic surfactants falling within the scope of the invention include Neodol 23-6.5, Neodol 25-7, Dobanol 45-4, Dobanol 45-7, Dobanol 45-9, Dobanol 91-2.5, Dobanol 91-3, Dobanol 91-4, Dobanol 91-6, Dobanol 91-8, Dobanol 23-6.5, Synperonic 6, Synperonic 14, the condensation products of coconut alcohol with an average of between 5 and 12 moles of ethylene oxide per mole of alcohol, the coconut alkyl portion having from 10 to 14 carbon atoms, and the condensation products of tallow alcohol with an average of between 7 and 12 moles of ethylene oxide per mole of alcohol, the tallow portion containing between 16 and 22 carbon atoms. Secondary linear alkyl ethoxylates are also suitable in the present compositions, especially those ethoxylates of the Tergitol series having from about 9 to 15 carbon atoms in the alkyl group and up to about 11, especially from about 3 to 9, ethoxy residues per molecule. Especially preferred nonionic surfactants of this class are Neodol 23-6.5 which is $C_{12}$–$C_{13}$ linear alcohol ethoxylated with an average of 6.7 moles of ethylene oxide per mole of alcohol and has a molecular weight of 488 g/mole and Neodol 25-7 which is $C_{12}$–$C_{15}$ linear alcohol ethoxylated with an average of 7.3 moles of ethylene oxide and has a molecular weight of 524 g/mole. Surface tensions for 0.1% solutions of Neodol 23-6.5 and Neodol 25-7 at 76° F. in distilled water are respectively 28 dynes/cm and 30 dynes/cm.

Another class of nonionic surfactants consists of the polyethylene oxide condensates of alkyl phenols, e.g., the condensation products of alkyl phenols having an alkyl group containing from 6 to 20 carbon atoms, in either a straight chain or branched chain configuration, with ethylene oxide, the said ethylene oxide being present in amounts equal to 4 to 50 moles of ethylene oxide per mole of alkyl phenol. Preferably the alkyl phenol contains about 8 to 18 carbon atoms in the alkyl group and about 6 to 15 moles of ethylene oxide per mole of alkyl phenol. The alkyl substituent in such compounds may be derived, for example, from polymerized propylene, di-isobutylene, octene and nonene. Other examples include dodecylphenol condensed with 9 moles of ethylene oxide per mole of phenol; dinonylphenol condensed with 11 moles of ethylene oxide per mole of phenol; nonylphenol and di-isooctylphenol condensed with 13 moles of ethylene oxide.

Another class of nonionic surfactants are the ethoxylated alcohols or acids or the polyoxypropylene, polyoxyethylene condensates which are capped with propylene oxide, butylene oxide, and/or short chain alcohols and/or short chain fatty acids, e.g., those containing from 1 to about 5 carbon atoms, and mixtures thereof.

Another class of nonionic surfactants are semi-polar nonionic surfactants including water-soluble amine oxides containing one alkyl moiety of from about 10 to 18 carbon atoms and two moieties selected from the group of alkyl and hydroxyalkyl moieties of from about 1 to about 3 carbon atoms; water-soluble phosphine oxides containing one alkyl moiety of about 10 to 18 carbon atoms and two moieties selected from the group consisting of alkyl groups and hydroxyalkyl groups containing from about 1 to 3 carbon atoms; and water-soluble sulfoxides containing one alkyl moiety of from about 10 to 18 carbon atoms and a moiety selected from the group consisting of alkyl and hydroxyalkyl moieties of from about 1 to 3 carbon atoms.

Ampholytic surfactants include derivatives of aliphatic, or aliphatic derivatives of heterocyclic, secondary and tertiary amines in which the aliphatic moiety can be straight chain or branched and wherein one of the aliphatic substituents contains from about 8 to 18 carbon atoms and at least one aliphatic substituent contains an anionic water-solubilizing group.

Zwitterionic surfactants includes derivatives of aliphatic quaternary ammonium, phosphonium, and sulfonium compounds in which one of the aliphatic substituents contains from about 8 to 18 carbon atoms.

Useful anionic surfactants include water-soluble salts of the higher fatty acids, i.e., soaps. These include alkali metal soaps such as the sodium, potassium, ammonium, and alkylolammonium salts of higher fatty acids containing from about 8 to about 24 carbon atoms, and preferably from about 12 to about 18 carbon atoms. Soaps can be made by direct saponification of fats and oils or by the neutralization of free fatty acids. Particularly useful are the sodium and potassium salts of the mixtures of fatty acids, derived from coconut oil and tallow, i.e., sodium or potassium tallow and coconut soap.

Useful anionic surfactants also include the water-soluble salts, preferably the alkali metal, ammonium and alkylolammonium salts, of organic sulfuric reaction products having in their molecular structure an alkyl group containing from about 10 to about 20 carbon atoms and a sulfonic acid or sulfuric acid ester group. (Included in the term "alkyl" is the alkyl portion of acyl groups.) Examples of this group of synthetic surfactants are the sodium and potassium alkyl sulfates, especially those obtained by sulfating the higher alcohols ($C_8$–$C_{18}$ carbon atoms such as those produced by reducing the glycerides of tallow or coconut oil; and the sodium and potassium alkylbenzene sulfonates in which the alkyl group contains from about 9 to about 15 carbon atoms, in straight chain or branched chain configuration, e.g., those of the type described in U.S. Pat. Nos. 2,220,099 and 2,477,383. Especially valuable are linear straight chain alkylbenzene sulfonates in which the average number of carbon atoms in the alkyl group is from about 11 to 13, abbreviated as $C_{11}$–$C_{13}$ LAS.

Other anionic surfactants herein are the sodium alkyl glyceryl ether sulfonates, especially those ethers of higher alcohols derived from tallow and coconut oil; sodium coconut oil fatty acid monoglyceride sulfonates and sulfates; sodium or potassium salts of alkyl phenol ethylene oxide ether sulfates containing from about 1 to about 10 units of ethylene oxide per molecule and wherein the alkyl groups contain from about 8 to about 12 carbon atoms; and sodium or potassium salts of alkyl ethylene oxide ether sulfates containing about 1 to about 10 units of ethylene oxide per molecule and wherein the alkyl group contains from about 10 to about 20 carbon atoms.

Other useful anionic surfactants herein include the water-soluble salts of esters of alpha-sulfonated fatty acids containing from about 6 to 20 carbon atoms in the fatty acid group and from about 1 to 10 carbon atoms in the ester group; water-soluble salts of 2-acyloxyalkane-1-sulfonic acids containing from about 2 to 9 carbon atoms in the acyl group and from about 9 to about 23 carbon atoms in the alkane moiety; water-soluble salts of olefin and paraffin sulfonates containing from about 12 to 20 carbon atoms; and beta-alkyloxy alkane sulfonates containing from about 1 to 3 carbon atoms in the alkyl group and from about 8 to 20 carbon atoms in the alkane moiety.

Cationic surfactants herein comprise a wide variety of compounds characterized by one or more organic hydrophobic groups in the cation and generally by a quaternary nitrogen associated with an acid radical. Pentavalent nitrogen ring compounds are also considered quaternary nitrogen compounds. Suitable anions are halides, methyl sulfate and hydroxide. Tertiary amines can have characteristics similar to cationic surfactants at solution pH values less than about 8.5. A more complete disclosure of these and other cationic surfactants useful herein can be found in U.S. Pat. No. 4,228,044, Cambre, issued Oct. 14, 1980, incorporated herein by reference.

As previously indicated, the surface active agent is preferably applied to the cellulosic fibers prior to the crosslinking reactions with $C_2$–$C_9$ polycarboxylic acid crosslinking agent occurring. Very preferably, the individualized, crosslinked cellulosic fibers with surface active agent thereon are prepared in a process comprising curing uncrosslinked cellulosic fibers with from 1% to 15%, preferably 3% to 12%, $C_2$–$C_9$ polycarboxylic acid crosslinking agent, by weight, on a citric acid basis applied on a dry fiber basis, and from 0.005% to 1%, preferably from 0.01% to 0.2%, surface active agent, by weight, applied on a dry fiber basis, thereon, to cause the polycarboxylic acid crosslinking agent to react with the cellulosic fibers and form ester crosslinks between cellulose molecules, to form said crosslinked cellulosic fibers with surface active agent thereon, without washing of the crosslinked fibers or bleaching and washing of the crosslinked fibers.

We turn now in more detail to the aforementioned very preferred process where uncrosslinked cellulosic fibers with from 1% to 15%, preferably from 3% to 12%, of $C_2$–$C_9$ polycarboxylic acid crosslinking agent, by weight, on a citric acid basis applied on a dry fiber basis, and from 0.005% to 1%, preferably from 0.01% to 0.2%, surface active agent, by weight, applied on a dry fiber basis, thereon, are heated to remove any moisture content and to cause the polycarboxylic acid crosslinking agent to react with the cellulosic fibers and form ester crosslinks between cellulose molecules, i.e., to cause curing, to form the crosslinked fibers with surface active agent thereon which are the essential component of the fluid acquisition and distribution member herein. This step is readily carried out on uncrosslinked cellulosic fibers having moisture content ranging from 0% to about 70%, preferably ranging from 30% to 40%, in unrestrained form or in sheet form.

In the case of treating fibers in unrestrained form, e.g., defibrated (fluffed) fibers, a moisture content removal portion of the heating step may be carried out in a first apparatus to dry to a consistency ranging from 60% to 100%, e.g., 90%, by a method known in the art as flash drying. This is carried out by transporting the fibers in a hot air stream, e.g., at an introductory air temperature ranging from 200° F. to 750° F., preferably at an introductory air temperature ranging from 300° F. to 550° F., until the target consistency is reached. This imparts additional twist and curl to the fibers as water is removed from them. While the amount of water removed by this drying step may be varied, it is believed that flash drying to the higher consistencies in the 60% to 100% range provides a greater level of fiber twist and curl than does flash drying to a consistency in the low part of the 60%–100% range. In the preferred embodiments, the fibers are dried to about 85%–95% consistency. Flash drying the fibers to a consistency, such as 85%–95%, in a higher portion of the 60%–100% range reduces the amount of drying which must be accomplished following flash drying. The subsequent portion of the heating step, or all of the heating step if flash drying is omitted, can involve heating for a period ranging from 5 seconds to 2 hours at a temperature ranging from 120° C. to 280° C. (air temperature in the heating apparatus), preferably at a temperature ranging from 145° to 190° C. (air temperature in the heating apparatus) for a period ranging from 2 minutes to 60 minutes in continuous air-through drying/curing apparatus (heating air is passed perpendicularly through a traveling bed of fibers) or in a static oven (fibers and air maintained stationary in a container with a stationary heating means), or other heating apparatus, to remove any remaining moisture content and to cause crosslinking reactions to occur which stiffen the fibers as a result of intrafiber crosslinking. The heating should be such that the temperature of the fibers does not exceed about 227° C. (440° F.) since the fibers can burst into flame at this temperature. The admixture is heated for an effective period of time to remove any remaining moisture content and to cause the crosslinking agent to react with the cellulosic fibers. The extent of reaction depends upon the dryness of the fiber, the time in the heating apparatus, the air temperature in the heating apparatus, pH, amount of catalyst and crosslinking agent and the method used for heating. Crosslinking at a particular temperature will occur at a higher rate for fibers of a certain initial moisture content with continuous, air-through drying/curing than with drying/curing in a static oven. Those skilled in the art will recognize that a number of temperature-time relationships exist. Temperatures from about 145° C. to about 165° C. (air temperature in the heating apparatus) for periods between about 30 minutes and 60 minutes, under static atmosphere conditions will generally provide acceptable drying/curing efficiencies for fibers having moisture contents less than about 10%. Those skilled in the art will also appreciate that higher temperatures and forced air convection (air-through heating) decrease the time required. Thus, temperatures ranging from about 170° C. to about 190° C. (air temperature in the heating apparatus) for periods between about 2 minutes and 20 minutes, in an air-through oven will also generally provide acceptable drying/curing efficiencies for fibers having moisture contents less than 10%.

In an alternative for completing heating after an initial flash drying step, flash drying and curing are carried out or curing only is carried out if the prior flash drying provides 100% consistency effluent, by routing the effluent from the flash drier (at 90% to 100% consistency) to a cyclone separator which separates air from the air/fiber admixture from the flash drier, discharging the fibers from the cyclone separator into a stream of hot air (e.g., 400° F.) in a duct containing at least one U-shaped portion, which carries the fibers through the duct thereby providing a travel path which provides sufficient residence time to cause removal of any moisture content and to cause esterification reaction to occur between fibers and the $C_2$–$C_9$ polycarboxylic acid, and discharging from the duct into a cyclone separator to separate the esterified fibers, and if necessary or desired, causing additional crosslinking to occur, e.g., in a subsequent air-through oven or static oven. Apparatus for the initial flash drying step may also be the same kind of apparatus as described herein (a cyclone separator, hot air treatment duct and cyclone separator), so that two or more sets for such apparatus are used in series as required by the need to bring in fresh dry air over the course of drying and curing.

The resulting crosslinked fibers (i.e., produced in any of the alternatives described above for application of the heating step to fibers in unrestrained form) are optionally moisturized, e.g., by spraying with water to provide 5% to 15% moisture content. This makes the fibers more resistant to damage that is of risk to occur due to subsequent handling or due to processing in making absorbent products from the fibers.

We turn now to the case where the heating step is carried out on the fibers in sheet form to dry the fibers and to cause the crosslinking reactions to occur. The same times and temperatures are applicable as described above for fibers in unrestrained form. Preferably, the heating is carried out at 145° C. to 190° C. (air temperature in the heating apparatus) for 2 to 60 minutes. After curing, the crosslinked fibers are optionally moisturized to 5% to 15% moisture content to provide resistance to damage from handling and optionally converted into substantially individualized form. The conversion to individualized form may be carried out utilizing a commercially available disc refiner or by treatment with fiber fluffing apparatus, such as the one described in U.S. Pat. No. 3,987,968, incorporated herein by reference. An effect of curing in sheet form is that fiber-to-fiber bonding restrains the fibers from twisting and curling compared to where individualized crosslinked fibers are made with curing under substantially unrestrained conditions. The fibers made in this way would be expected to provide structures exhibiting less absorbency and wettability than in the case of the fibers cured in unrestrained form.

We turn now to a method for forming input material for the heating step. This at minimum comprises contacting uncrosslinked fibers with aqueous crosslinking composition consisting essentially of $C_2$–$C_9$ polycarboxylic acid crosslinking agent and surface active agent.

The contacting is carried out on uncrosslinked fibers with an aqueous crosslinking composition which contains $C_2$–$C_9$ polycarboxylic acid crosslinking agent and surface active agent to obtain uniform distribution of the aqueous crosslinking composition on the fibers.

The aqueous crosslinking composition contains $C_2$–$C_9$ polycarboxylic acid crosslinking agent in an amount so as to provide from 1% to 15%, preferably from 3% to 12%, thereof, by weight, on a citric acid basis applied on a dry fiber basis, on the fibers subjected to the heating step and surface active agent in an amount so as to provide from 0.005% to 1%, preferably from 0.01% to 0.2%, thereof, by weight, on a dry fiber basis, on the fibers subjected to the heating step.

The lower limit on surfactant presumes that not more than 90% of the surfactant will be removed during the heating step or in other steps subsequent to the heating step and prior to use of the crosslinked surface active agent coated fibers in the fluid acquisition and distribution member herein.

The pH for the aqueous crosslinking composition can be, for example, 1 to 5.0. The pHs below 1 are corrosive to the processing equipment. The pHs above 5 provide an impractically low reaction rate. The esterification reaction will not occur at alkaline pH. Increasing pH reduces reaction rate. The pH very preferably ranges from 2 to 3.5. The pH is readily adjusted upward if necessary by addition of base, e.g., sodium hydroxide.

Catalyst is preferably included in said aqueous crosslinking composition to speed up the crosslinking reaction and protect brightness. The catalyst can be any which catalyzes the crosslinking reactions. Applicable catalysts include, for example, alkali metal hypophosphites, alkali metal phosphites, alkali metal polyphosphates, alkali metal phosphates, and alkali metal sulfates. Especially preferred catalysts are the alkali metal hypophosphites, alkali metal polyphosphates, and alkali metal sulfates. The mechanism of the catalysis is unknown, although the catalysts may simply be functioning as buffering agents, keeping the pH levels within the desired ranges. A more complete list of catalysts useful herein can be found in Welch et al., U.S. Pat. No. 4,820,307, issued April 1989, incorporated herein by reference. The selected catalyst may be utilized as the sole catalyzing agent, or in combination with one or more other catalysts. The amount of catalyst preferably utilized is, of course, dependent upon the particular type and amount of crosslinking agent and the reaction conditions for curing, especially temperature and pH. In general, based upon technical and economic considerations, catalyst levels of between about 5 wt. % and about 80 wt. %, based on the weight of crosslinking agent added to the cellulosic fibers, are preferred. For exemplary purposes, in the case wherein the catalyst utilized is sodium hypophosphite and the crosslinking agent is citric acid, a catalyst level of about 25 wt. %, based upon the amount of citric acid added, is preferred.

In a very preferred method, said contacting is carried out by transporting a sheet of uncrosslinked high lignin content cellulosic fibers having a moisture content ranging from 0% to 10% through a body of said aqueous crosslinking composition contained in a nip of press rolls (e.g., rolls 1 foot in diameter and 6 feet wide) and through said nip to impregnate said sheet of fibers with said aqueous crosslinking composition and to produce on the outlet side of the nip an impregnated sheet of fibers containing said aqueous crosslinking composition in an amount providing 30% to 80% or more (e.g., even up to 85% or 90% or even 95%), preferably 40% to 70%, consistency. The time of the sheet of fibers in the body of aqueous crosslinking composition as determined by the rotation speed of the press rolls, and the pressure of the rolls on the sheet of fibers passing therethrough, are regulated so that the appropriate consistency and amount of aqueous crosslinking composition as specified above, are obtained. A typical pressure at the nip of the press rolls is 45 psi and 45 lbs per linear inch. The press roll speed is normally regulated to provide a time of the sheet of uncrosslinked fibers in the body of aqueous crosslinking composition ranging from 0.005 to 60 seconds, preferably from 0.05 to 5 seconds. In a less preferred alternative, the sheet of uncrosslinked fibers is impregnated with aqueous crosslinking composition to provide the aforementioned consistencies, by spraying. In either case, the liquid content of the impregnated sheet is optionally adjusted by mechanically pressing and/or by air drying.

The impregnated sheet of fibers is preferably subjected to defibration prior to treatment in the heating step. Defibration is preferably performed by a method wherein knot and pill formation and fiber damage are minimized. Typically, a commercially available disc refiner is used. Another type of device which has been found to be useful for defibrating the cellulosic fibers is the three stage fluffing device described in U.S. Pat. No. 3,987,968, issued to D. R. Moore and O. A. Shields on Oct. 26, 1976, said patent being hereby expressly incorporated by reference into this disclosure. The fluffing device described in U.S. Pat. No. 3,987,968 subjects moist cellulosic pulp fibers to a combination of mechanical impact, mechanical agitation, air agitation and a limited amount of air drying to create a substantially knot-free fluff. Other applicable methods of defibration include, but are not limited to, treatment in a Waring blender, tangentially contacting the fibers with a rotating wire brush and hammermilling. Preferably, an air stream is directed toward the fibers during such defibration to aid in separating the fibers into substantially individualized form. Regardless of the particular mechanical device used to form the fluff, the fibers are preferably mechanically treated while initially containing between about 40% and 70% moisture. The individualized fibers have imparted thereto an enhanced degree of curl and twist relative to the amount of curl and twist naturally present in such fibers. It is believed that this additional curl and twist enhances the resilient character of structures made from the crosslinked fibers. The result of the defibrating is referred to herein as the defibrated admixture. The defibrated admixture is ready for the heating step. The impregnated sheet may be treated, for example, in a prebreaker (e.g., a screw conveyor) to disintegrate it, before defibration.

In a less preferred alternative, the impregnated sheet of fibers is treated in the heating step without prior disintegration as described above, to produce a sheet of crosslinked cellulosic fibers, which optionally is subjected to defibration after the heating step.

Contacting the uncrosslinked cellulosic fibers with aqueous crosslinking composition may also be carried out by forming a slurry of the uncrosslinked fibers in unrestrained form in the aqueous crosslinking composition, of consistency ranging from 0.1% to 20%, very preferably from 2% to 15%, and maintaining the slurry for about 1 to 240 minutes, preferably for 5 to 60 minutes. The slurry can be formed, e.g., by causing a sheet of drylap to disintegrate by agitating it in the aqueous crosslinking composition.

A liquid removal step is normally next carried out to increase the consistency to one suitable for the heating step.

This is preferably carried out by dewatering (removing liquid) to provide a consistency ranging from about 30% to 80%, very preferably ranging from about 40% to 50%, and optionally thereafter drying further.

For exemplary purposes, dewatering may be accomplished by such methods as mechanically pressing or centrifuging. The product of the dewatering is typically denoted cake.

We turn now to the step wherein the cake may be dried further. This is typically carried out to provide a consistency within about a 35% to 80% consistency range, preferably to provide a consistency ranging from 50% to 70%, and is preferably performed under conditions such that utilization of high temperature for an extended period of time is not required, e.g., by a method known in the art as air drying. Excessively high temperature and time in this step may result in drying the fibers beyond 80% consistency, thereby possibly producing an undesired amount of fiber damage during an ensuing defibration.

The term "the liquid-reduced admixture" as used herein refers to the product of the liquid removal step.

The liquid-reduced admixture is typically subjected to defibration performed as described above in respect to an impregnated sheet except that the liquid-reduced admixture is subjected to defibration in place of the impregnated sheet. The result of the defibrating is referred to herein as the defibrated admixture.

The defibrated admixture or the liquid-reduced admixture in the case where defibration is omitted, is ready for the heating step.

The cured product should not be subjected to steps which would cause significant removal of the surfactant which remains on the crosslinked fibers, e.g., washing or bleaching and washing steps.

We turn now to the embodiment of a disposable absorbent article comprising a liquid pervious topsheet, a liquid impervious backsheet and an absorbent core positioned between said topsheet and said backsheet, said absorbent core comprising (i) the fluid acquisition and distribution member herein with top surface adjacent said topsheet and a bottom surface and (ii) a fluid storage member having a top surface in contact with bottom surface of the fluid acquisition and distribution member and comprising discrete particles of absorbent gelling material.

A preferred execution in the form of a medium size disposable diaper for a male baby is described in conjunction with FIG. 1. With reference to FIG. 1, a disposable diaper 10 has a liquid pervious topsheet 12 (which is partially broken away to show the interior elements), and a liquid impervious backsheet 14 with an absorbent core disposed between them consisting of a fluid acquisition and distribution member 16 and a fluid storage member 18. The fluid acquisition and distribution member 16 is rectangular in top view. The fluid storage member 18 is hourglass-shaped in top view. The fluid acquisition and distribution member 16 is positioned on top of the fluid storage member 18 with its longitudinal centerline positioned along the longitudinal centerline of the fluid storage member and closer to the front waist than to the rear waist. The fluid acquisition and distribution member 16 is 3 inches by 10 inches by about one-fourth inch and has its edge closest to the front waist positioned about 2 to 3 inches back of the front waist. The fluid storage member 18 is symmetrically disposed between the topsheet 12 and the backsheet 14 and is 5 inches wide at the crotch and 10½ inches wide at its lateral edges and has its lateral edges spaced downwardly about an inch from the front and back waist (lateral edges of the topsheet and backsheet). In this execution, the area of the top surface of the fluid acquisition and distribution member 16 is about one-third that of the area of top surface of the fluid storage member 18.

This is only exemplary of one execution of disposable absorbent article for which the invention herein finds application.

In general, the fluid acquisition and distribution member should encompass the vicinity of the area of discharge of body fluids. For disposable diapers, these areas would include the crotch area and preferably for males, also the region where urination discharges occur in front of the diaper (i.e., the portion of the diaper intended to be placed on the front of the wearer).

As indicated above, the fluid acquisition and distribution member preferably has a top surface with an area which is less than the area of the top surface of the fluid storage member, very preferably which has a top surface with an area which is about 15% to 95% of the top surface of the fluid storage member, most preferably which has a top surface with an area which is about 20% to 50% of the top surface of the fluid storage member.

The fluid acquisition and distribution member can be any desired shape consistent with functional fit and the goals discussed above. These shapes include, for example, circular, rectangular, trapezoidal or oblong, e.g., hourglass-shaped, dog-bone-shaped, half dog-bone-shaped, oval or irregularly shaped.

The fluid storage member can be any desired shape consistent with functional fit including those shapes recited above for the fluid acquisition and distribution member.

While FIG. 1 depicts a diaper where the fluid acquisition and distribution member and the fluid storage member have different shapes, these also can have the same or similar shapes.

The backsheet of the articles herein can be constructed, for example, from a thin, plastic film of polyethylene, polypropylene, or other flexible moisture impeding material which is substantially water impervious. Polyethylene, having an embossed caliper of approximately 1.5 mils, is especially preferred.

The topsheet of the articles herein can be made in part or completely of synthetic fibers or films comprising such materials as polyester, polyolefin, rayon, or the like, or of natural fibers such as cotton. In nonwoven topsheets, the fibers are typically bound together by a thermal binding procedure or by a polymeric binder such as polyacrylate. This sheet is substantially porous and permits a fluid to readily pass therethrough into the underlying absorbent core.

Another suitable type of topsheet comprises the topsheets formed from liquid impervious polymeric material such as polyolefins. Such topsheets can have tapered capillaries of certain diameter and taper positioned in the topsheet to permit flow of discharged fluid through the topsheet into the underlying absorbent core of the article.

Topsheet construction is generally disclosed in Davidson, U.S. Pat. No. 2,905,117, Issued Sep. 22, 1959; Del Guercio, U.S. Pat. No. 3,063,452, Issued Nov. 13, 1962; Holliday, U.S. Pat. No. 3,113,570, Issued Dec. 10, 1963, and Thompson, U.S. Pat. No. 3,929,135; Issued Dec. 30, 1975; which patents are incorporated herein by reference. Preferred topsheets are constructed from polyester, rayon, rayon/polyester blends, polyethylene or polypropylene. The topsheet can be treated with surfactant to make it more wettable and therefore relatively less hydrophobic, to thereby increase fluid flow through it at least upon initial wetting. However, the topsheet should still be more hydrophobic than the absorbent article element which receives fluids after passing through the topsheet.

The fluid acquisition and distribution member is described in detail above. Preferably, it is entirely composed of the individualized, crosslinked cellulosic fibers having a $C_2$–$C_9$ polycarboxylic acid crosslinking agent reacted therein in an intrafiber ester crosslink bond form providing a water retention value of from about 25 to 60 and having uniformly distributed thereon from about 0.0005% to 1%, very preferably from 0.001% to 0.2%, by weight, on a dry fiber basis, of surface active agent. It can contain amounts of other materials which do not substantially detract from its ability to acquire fluids and release such to an adjacent storage member. Thus, preferably, it is free of absorbent gelling material, i.e., contains no more than about 2.0% of absorbent gelling material, very preferably less than about 1.0% of absorbent gelling material, most preferably, zero or essentially zero (less than 0.5%) absorbent gelling material.

The fluid acquisition and distribution member is readily prepared as followed. A bale of fibers as described above is run through a disc refiner to fluff the material to produce individual fibers which are air-laid on a foraminous belt moving past a suction drum to produce appropriate shaped members. If density adjustment of the resulting body is necessary, it is readily carried out using a hydraulic press.

The fluid storage member comprises 15% to 100%, by weight, preferably at least 25% of absorbent gelling material and from 0% to 85% of carrier material.

The absorbent gelling material can be in the form of discrete particles or in the form of fibrous material or in any other form which can be incorporated into a flexible web or sheet to form the storage member.

The superabsorbent materials for use in the storage layer are those which are capable of absorbing at least 10 gms of a 1.0% NaCl aqueous solution prepared using distilled water per gram of absorbent gelling material as determined according to the Absorbent Capacity Test Method described in U.S. Pat. No. 5,217,445, incorporated herein by reference.

The absorbent gelling material which is employed in the storage layer of the absorbent core will most often comprise a substantially water-insoluble, slightly crosslinked, partially neutralized, polymeric absorbent gelling material. This material forms a hydrogel upon contact with water. Such polymer materials can be prepared from polymerizable, unsaturated, acid-containing monomers. Suitable unsaturated acidic monomers for use in preparing the polymeric gelling material include those listed in Brandt/Goldman/Inglin U.S. Pat. No. 4,654,039, issued Mar. 31, 1987, and reissued as U.S. Pat. No. RE 32,649 on Apr. 19, 1988, both incorporated herein by reference. Preferred monomers include acrylic acid, methacrylic acid, and 2-acrylamido-2-methyl propane sulfonic acid. Acrylic acid itself is especially preferred for preparation of the polymeric gelling agent material.

The polymeric component formed from unsaturated, acid-containing monomers may be grafted onto other types of polymer moieties such as starch or cellulose.

Preferred polymeric absorbent gelling materials which can be prepared from conventional types of monomers include hydrolyzed acrylonitrile grafted starch, polyacrylate grafted starch, polyacrylates, maleic anhydride-based copolymers and combinations thereof.

Especially preferred are the polyacrylates and polyacrylate grafted starch.

The polymeric absorbent gelling materials will in general be slightly cross-linked. Cross-linking serves to render the hydrogel-forming polymer gelling agents substantially water-insoluble, and crosslinking thus in part determines the gel volume and extractable polymer characteristics of the hydrogels formed from the polymeric gelling agents employed. Suitable crosslinking agents are well known in the art and include, for example, those described in greater detail in Masuda et al, U.S. Pat. No. 4,076,663, issued Feb. 28, 1978, incorporated herein by reference. Preferred crosslinking agents are the di- or polyesters of unsaturated mono- or polycarboxylic acids with polyols, the bisacrylamides and the di- or triallyl amines. Other preferred crosslinking agents are N,N'-methylenebisacrylamide, trimethylol propane triacrylate and triallyl amine. The crosslinking agent can generally constitute from about 0.001 mole % to 3 mole % of the hydrogel-forming polymeric gelling material particles.

The polymeric absorbent gelling materials are generally employed in partially neutralized form. For use herein, such materials are considered partially neutralized when at least 25 mole %, and preferably at least 50 mole % of monomers used to form the polymer are acid group-containing monomers which have been neutralized with a salt-forming cation. Suitable salt-forming cations include alkali metal, ammonium, substituted ammonium and amines. This percentage of the total monomers utilized which are neutralized acid group-containing monomers is referred to as the "degree of neutralization."

When the absorbent gelling material is used in the form of discrete particles of absorbent gelling material, it is used in conjunction with nonsuperabsorbent carrier material, e.g., fibrous carrier material, including cellulose fibers, in the form of fluff, such as is conventionally used in absorbent cores. Modified cellulose fibers can also be used but preferably are not used. Synthetic fibers can be used and include those made of cellulose acetate, polyvinyl fluoride, polyvinylidene chloride, acrylics (such as Orlon), polyvinyl acetate, non-soluble polyvinyl alcohol, polyethylene, polypropylene, polyamides (such as nylon), polyesters, bicomponent fibers, tricomponet fibers, mixtures thereof and the like. Preferred synthetic fibers have a denier of from about 3 denier per filament to about 25 denier per filament, more preferably from about 5 denier per filament to about 16 denier per filament. Also preferably, the fiber surfaces are hydrophilic or are treated to be hydrophilic.

The average dry density of the fluid storage member comprising discrete particles of absorbent gelling material and carrier material will generally be in the range of from about 0.06 to about 0.5 g/cm$^3$, and more preferably within the range of from about 0.10 to about 0.4 g/cm$^3$, even more preferably from about 0.15 to about 0.3 g/cm$^3$, most preferably from about 0.15 to about 0.25 g/cm$^3$. Typically the basis weight of the fluid storage member can range from about 0.02 to 0.12 g/cm$^2$, more preferably from about 0.04 to 0.08 g/cm$^2$, most preferably from about 0.05 to 0.07 g/cm$^2$. This type of fluid storage member can be substantially homogeneous (i.e., having the same density and basis weight throughout and having the absorbent gelling material distributed uniformly therethrough) or contain regions of relatively higher and relatively lower density and basis weight or can have an absorbent gelling material gradient with more absorbent gelling material in regions of high fluid handling requirements and less absorbent gelling material at lower demand regions.

The fluid storage member embodiments comprising fibrous carrier means can be formed by a process comprising air laying a substantially dry mixture of fibers and absorbent gelling material particles and, if desired or necessary, densifying the resulting web. Such a procedure is in general described more fully in the hereinbefore referenced Weisman and Goldman U.S. Pat. No. 4,610,678, issued Sep. 9, 1986, incorporated herein by reference. These fluid storage member embodiments can also be formed by metering absorbent gelling material from a hopper onto fluff (e.g., obtained by disc refining of drylap) on a belt and moving the belt adjacent a suction drum containing pockets to suction the admixture into the pockets to form the admixture into the shape of the pockets.

We turn now to the case where fibers of absorbent gelling material are used instead of discrete particles of absorbent gelling material. These kind of fibers are described in *Textile Science and Technology*, Volume 7, Pronoy K. Chatterjee, editor, Elsevier Science Publishers B.V. (The Netherlands), 1985, in Chapters VII and VIII (collectively pages 217–280), incorporated by reference herein.

One type of absorbent gelling material fiber comprises the polycarboxylate polymer-modified cellulosic fibrous pulps such as mildly hydrolyzed methyl acrylate-grafted softwood kraft pulps. These superabsorbent fibers are described in U.S. Ser. No. 07/378,154, filed Jul. 11, 1989, titled "Absorbent Paper Comprising Polymer-Modified Fibrous Pulps and Wet-Laying Process for the Production Thereof," by Larry N. Mackey and S. Ebrahim Seyed-Rezai, incorporated herein by reference.

Other types of absorbent gelling material fibers can include crosslinked carboxymethyl cellulose and polymer grafted cellulose fibers. Polymer grafted cellulose fibers include hydrolyzed polyacrylonitrile, polyacrylic esters, and polyacrylic and polymethacrylic acids. Discussion of these fibers and references to processes for making them, can be found in the Chatterjee's Vol. 7 of *Textile Science and Technology* as previously incorporated herein by reference. They are also discussed in A. H. Zahran, et al, "Radiation Grafting of Acrylic and Methacrylic Acid to Cellulose Fibers to Impart High Water Sorbency", J. of App. Polymer Science, Vol. 25, 535–542 (1980), which discusses radiation grafting of methacrylic acid and acrylic acid to cellulose fibers, as the title suggests; U.S. Pat. No. 4,036,588, J. L. Williams, et al, issued Jul. 19, 1977, which describes the graft copolymerization of a vinyl monomer containing a hydrophilic group onto cellulose-containing material, e.g., rayon yarn; and U.S. Pat. No. 3,838,077, H. W. Hoftiezer, et al, issued Sep. 24, 1974, which discloses polyacrylonitrile-grafted cellulose fibers. Each of the foregoing disclosures are incorporated herein by reference.

The absorbent gelling material fibers can be incorporated into webs of conventional or other nonsuperabsorbent fibers, such as in wetlaid webs or in airlaid webs. They can also be formed into nonwoven sheets; such sheets can consist essentially of absorbent gelling material fibers with or without carrier material. Nonwoven sheets made from absorbent gelling material fibers such as the non-acrylate superabsorbent microfibers and fibers useful for making such sheets are available from Arco Chemical Co. (Newtown Square, Pa., USA), under the tradename FIBERSORB™ and from Japan Exlan Co., Ltd. (Osaka, Japan) which markets absorbent gelling material fibers comprising a polyacrylonitrile core with a polyacrylic acid/polyammonium acrylate skin under the tradename LANSEAL™.

The fluid acquisition and distribution member is positioned on the fluid storage member by means known to those skilled in the art, e.g., suction belts and suction drums.

The invention is illustrated by the following examples.

REFERENCE EXAMPLE 1

Three hundred grams (on a bone dry basis, i.e., on a moisture-free basis) of southern softwood Kraft fibers in the form of drylap sheets is dispersed in aqueous solution containing 551.57 g of citric acid, 6.89 g of Pluronic® L35, 137.89 g of sodium hypophosphite, and 63 g of sodium hydroxide, by dipping and mixing, to form a slurry of 2.5% consistency. The fibers are soaked in the slurry for 30 minutes. This mixture is centrifuged to provide a dewatered cake of about 44% consistency. The dewatered cake, containing about 6% by weight citric acid (on a dry fiber basis) and 0.075% Pluronic® L35, on a dry fiber basis, is air dried to about 50% consistency. The air dried cake is fluffed in a disc refiner at a throughput rate of 180 g/min, flash dried to a consistency of 90% and heated for 6 minutes at an air temperature of 350° F. in an air-through oven and then air cooled with a fan to less than 150° F. There is no washing or bleaching after curing.

REFERENCE EXAMPLE 2

Reference Example 1 is duplicated except that the Pluronic® L35 is omitted.

EXAMPLE I

Reference Examples 1 and 2 are duplicated on a much larger scale and bales of citric acid crosslinked fibers with surfactant thereon and of citric acid crosslinked fibers without surfactant thereon are produced.

Testing results on fibers from the bales indicate for the citric acid crosslinked fibers with surfactant a 5K density of 0.11 g/cc, a drip capacity of 11.0 g/g, a wicking rate of 0.62 cm/s and a wet compressibility of 69 cc/g, and for the citric acid crosslinked fibers without surfactant a 5K density of 0.12 g/cc, a drip capacity of 12.4 g/g, a wicking rate of 0.89 cm/s and a wet compressibility of 6.9 cc/g. In each case the water retention value is about 35.

The fibers of each type are fluffed in a disc refiner and then are air-laid on a belt moving past a suction drum to form rectangular fluid acquisition and distribution members of 3 inches by 10 inches by about one-fourth inch, and in each case, the density is adjusted to 0.07 g/cc using a hydraulic press if not already at this level.

In the skin wetness test, use of fibers with surfactant is found to result in wetness in 4.1% of cases whereas use of fibers without surfactant is found to result in wetness in 11.7% of cases. The difference is found to be statistically significant at the 90% confidence level. The test results show a sustained effect, i.e., a benefit on overnight usage.

In the leakage rate test, use of fibers with surfactant is found to result in leakage in 2.82% of cases whereas use of fibers without surfactant is found to result in leakage in 6.99% of cases. The difference is not found to be statistically significant at least at the 90% confidence level because of the base size. A leakage rate of 2.82% is considered an excellent result.

In the acquisition rate test, use of fibers with surfactant is found to provide an acquisition potential Ao of 10.3 and an acquisition rate constant K of 127 whereas use of fibers without surfactant is found to provide an acquisition potential Ao of 10.2 and an acquisition rate constant K of 117. The results are the averages of 3–5 repetitions on different diapers.

In gush capacity testing, the fluid retained by the members at loading is set forth in Table 1 below.

TABLE 1

| Load | Fluid Retained By Member at Loading (g) | |
|---|---|---|
| (ml) | With Surfactant | Without Surfactant |
| 50 | 12.1 | 20.5 |
| 100 | 19.2 | 23.1 |
| 150 | 21.3 | 26.6 |
| 200 | 20.6 | 24.2 |
| 250 | 20.4 | 30.1 |
| 300 | 22.9 | 32.3 |
| 350 | 25.2 | 24.7 |
| 400 | 25.4 | 32.7 |

In gush capacity testing, the fluid retained by the members after 15 minutes is set forth in Table 2 below.

TABLE 2

| Load | Fluid Remaining in Member After 15 Minutes | |
|---|---|---|
| (ml) | With Surfactant | Without Surfactant |
| 50 | 1.0 | 9.4 |
| 100 | 4.5 | 17.6 |
| 150 | 9.5 | 18.9 |
| 200 | 11.1 | 20.1 |
| 250 | 12.4 | 22.3 |
| 300 | 14.2 | 30.4 |
| 350 | 20.4 | 24.2 |
| 400 | 19.4 | 32.1 |

Figure 2:
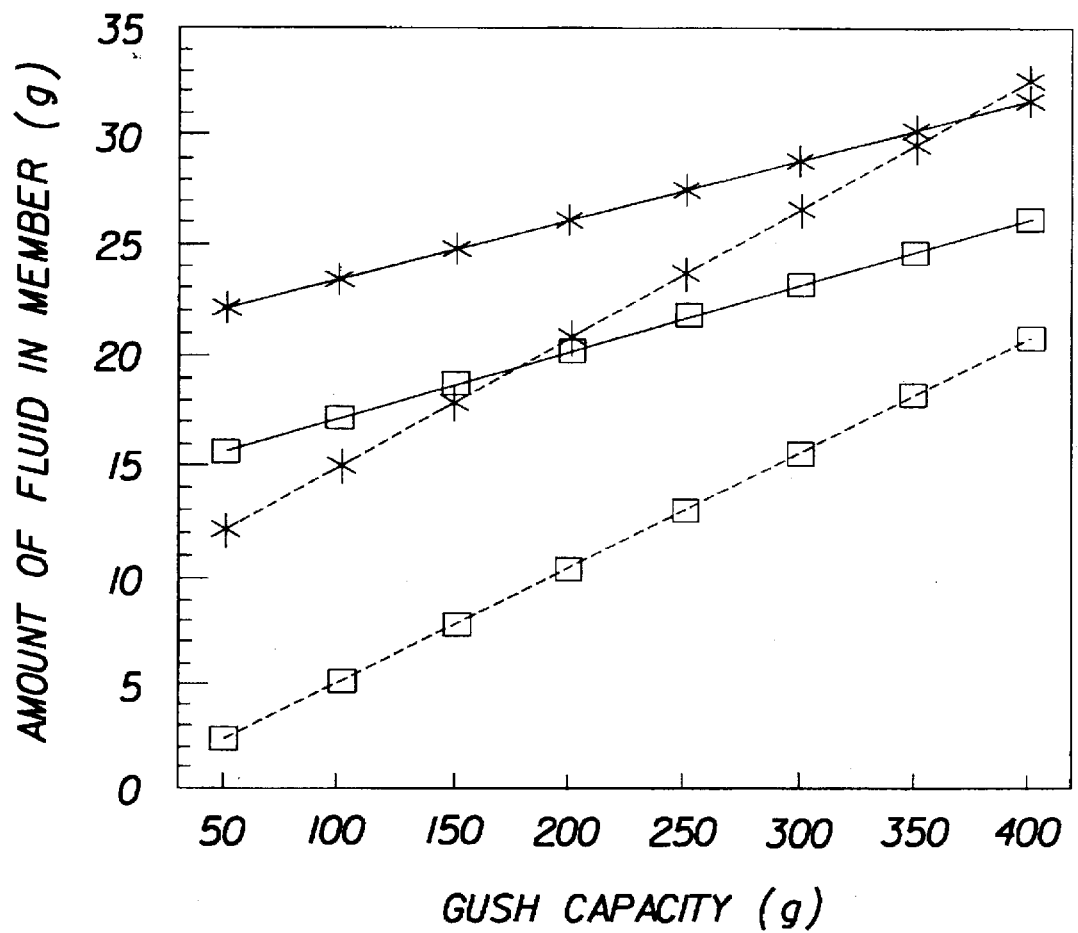
FIG. 2 is a graph of fluid retention versus load for gush capacity test results for the Example with the data being normalized by regression analysis.

The results of Tables 1 and 2 normalized by regression analysis are depicted in FIG. 2 wherein the continuous lines represent the results at loading and the dashed lines represent the results after 15 minutes and the lines with Xs denote no surfactant being used and the lines with squares denote surfactant being used.

The gush capacity test results show that the member without surfactant, initially as well as after 15 minutes, retains more fluid than the member with surfactant. This shows that the member with surfactant partitions fluid better (distributes it to an adjacent contacting storage layer better) than the member without surfactant and that the effect is a sustained effect. This is consistent with the dryness advantage (lower wetness percentage results) found in the skin wetness testing as indicated above.

EXAMPLE II

A disposable diaper is prepared comprising a thermally bonded polypropylene topsheet, a fluid impervious polyethylene backsheet, a fluid acquisition and distribution member composed of citric-acid-crosslinked fibers with Pluronic® L35 thereon under the topsheet and an hourglass shaped fluid storage member (comprising an air-laid mixture of conventional southern softwood Kraft fluff and sodium polyacrylate polymeric absorbent material of the type described in U.S. Pat. No. Reissue 32,649 and having an Absorbent Capacity in the Absorbent Capacity Test of about 30 g/g) positioned below the fluid acquisition and distribution member and above the backsheet. The diaper is similar in structure to that depicted in FIG. 1. The diaper provides excellent dryness and low incidence of leakage results on overnight usage on boy babies. Similar results of excellent dryness and low incidence of leakage are provided on overnight usage on girl babies where the diaper is the same as that described above except that the fluid acquisition and distribution member is 12 inches long and is symmetrically positioned with respect to the fluid storage layer.

Variations will be obvious to those skilled in the art. Therefore, the invention is defined by the claims.

What is claimed is:

1. A fluid acquisition and distribution member for use in a disposable, absorbent article, said member having a dry density ranging from 0.03 to 0.20 g/cc and consisting essentially of $C_2$–$C_9$ polycarboxylic acid crosslink cellulosic fibers, said fibers having substantially intra-fiber crosslinks, said fibers having an amount of a $C_2$–$C_9$ polycarboxylic acid crosslinking agent reacted therein in an intrafiber ester crosslink bond providing a water-retention volume from about 25 to 60 and having distributed thereon from about 0.005% to 1%, by weight, on the dry-fiber basis, of a surface-active agent.

2. The fluid acquisition and distribution member of claim 1, wherein the surface active agent is present on the fibers in an amount up to about 0.15%, by weight, on a dry fiber basis.

3. The fluid acquisition and distribution member of claim 1, wherein the individualized, crosslinked cellulosic fibers with the surface active agent thereon are prepared in a process comprising heating uncrosslinked cellulosic fibers with from 1% to 15% of the $C_2$–$C_9$ polycarboxylic acid crosslinking agent, by weight, on a citric acid basis, applied on a dry fiber basis, thereon, and from 0.005% to 1% of the surface active agent, by weight, applied on a dry fiber basis, thereon, to cause the polycarboxylic acid crosslinking agent to react with the cellulosic fibers and form ester crosslinks between cellulose molecules, and to form said crosslinked cellulosic fibers with the surface active agent thereon, without washing or bleaching and washing of the crosslinked fibers.

4. The fluid acquisition and distribution member of claim 3 wherein the surface active agent is a nonionic surfactant.

5. The fluid acquisition and distribution member of claim 4, wherein the non-ionic surfactant is one formed by condensing ethylene oxide with a base formed by condensation of propylene oxide with propylene glycol.

6. The fluid acquisition and distribution member of claim 5 wherein the non-ionic surfactant has a number average molecular weight ranging from about 1,000 to 5,000 grams/mole, the molecular weight of the poly(oxypropylene) unit ranges from 900 to 2,000 grams/mole, and contains from 10% to 80% of the poly(oxyethylene) unit by weight in the total molecule.

7. The fluid acquisition and distribution member of claim 6, wherein the non-ionic surfactant has a number average molecular weight of 1,900 grams/mole, the molecular weight of the poly(oxypropylene) unit is 950 grams/mole, and contains 50% of the poly(oxyethylene) unit by weight in the total molecule.

* * * * *